United States Patent [19]

Buxadé-Vinas

[11] Patent Number: 4,855,443

[45] Date of Patent: Aug. 8, 1989

[54] CHROMOGLYCIC ACID DERIVATIVE

[75] Inventor: Antonio Buxadé-Vinas, Barcelona, Spain

[73] Assignee: Laboratorios Vinas S. A., Barcelona, Spain

[21] Appl. No.: 224,573

[22] Filed: Jul. 26, 1988

[30] Foreign Application Priority Data

Aug. 5, 1987 [ES] Spain .................................. 8702294

[51] Int. Cl.⁴ ........................................... C07D 231/56
[52] U.S. Cl. ..................................... 548/372; 549/402
[58] Field of Search ......................................... 548/372

[56] References Cited

PUBLICATIONS

*Chemical Abstracts*, 82: 175230v (1975), [Fr. Demande 2,196,796, 3/22/74].
*Chemical Abstracts*, 82: 175231w (1975), [Fr. Demande 2,196,795, 3/22/74].

Primary Examiner—Richard A. Schwartz
Attorney, Agent, or Firm—Dressler, Goldsmith, Shore, Sutker & Milnamow

[57] ABSTRACT

An antiinflammatory derivative of chromoglycic acid having the formula

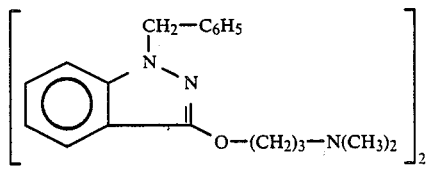
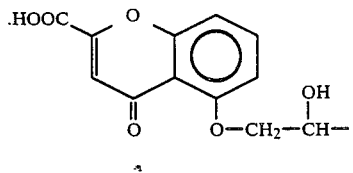
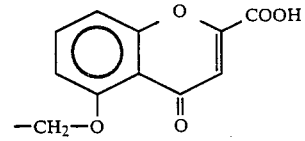

The process for the prepartion thereof is based on the reaction of chromoglycic acid, or a salt thereof, with benzidamine in a polar solvent.

1 Claim, No Drawings

CHROMOGLYCIC ACID DERIVATIVE

The invention relates to a chromoglycic acid derivative, particularly dibenzidamine chromoglycate having the structural formula (I)

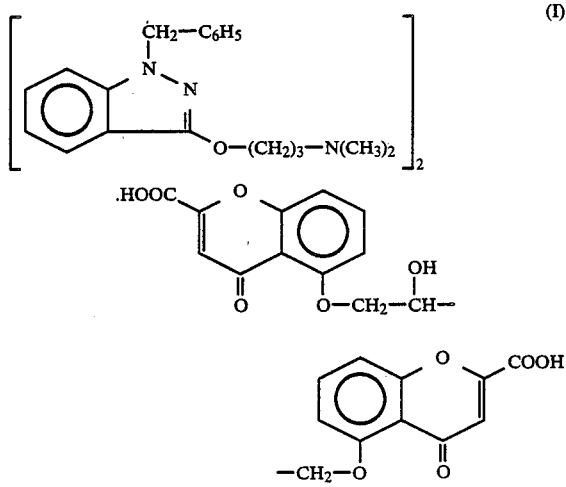

The invention also relates to a process for the preparation of said derivative.

The said process is characterised by reacting chromoglycic acid or an alkali salt thereof with benzidamine in the free base or strong acid salt form thereof, in a polar solvent.

Preferably the salt is the hydrochloride and the said solvent is water, a low molecular weight alcohol or acetone. The reaction temperature may reach the boiling point of the solvent.

Benzidamine is an amine, the full name of which is N,N-dimethyl-3-((1-(phenylmethyl)-1H-indazol-3-yl)oxy)-1-propanamine, which may give acid addition salts with strong acids such as the one to be found in commerce, the hydrochloride.

Chromoglycic acid is 1,3-bis(2-carboxy-4-oxo-5-chromenyloxy)-2-propanol acid, also available in commerce or in sodium salt form.

The derivative obtained affords advantages over other salts of chromoglycic acid or of benzidamine, on sharing in one same structure membrane stabilising and antiinflammatory properties respectively, thereby potentiating the antiinflammatory effect of benzidamine in immunity diseases, which does not occur in other chromoglycic acid or benzidamine derivatives.

With the use of the product obtained, inflammatory, immunity and allergy processes, covering a wide range of diseases may be treated, with a multiple action not described up to date.

The local tolerance has been studied in the rat, after topical application of the derivative, the product being observed to be well tolerated.

For therapeutic use, benzidamine chromoglycate may be administered without limitation topically, orally, via rectum or parenterally.

The active ingredient, dibenzidamine chromoglycate, according to the form of administration, will be found in an effective amount, depending on the necessary amounts of chromoglycic acid and benzidamine.

When the reaction medium is an organic solvent, any alkali or ammonium chloride formed is removed by filtration and the salt is obtained by evaporation of the organic solvent.

When the medium is aqueous, the salt is obtained by decantation.

The salt is obtained in the form of an amber coloured oil, which solidifies on subsequent removal of the solvent.

To facilitate the understanding, certain embodiments of the process are described hereinafter, to illustrate the invention without limitation.

EXAMPLE 1

A solution of 58.7 g of benzidamine hydrochloride in 300 ml of water was added slowly over a solution of 43.5 g of disodium chromoglycate in 400 ml of water. After stirring for one hour an ambar coloured oil was drawn off which, after decantation and drying gave 76.0 g of a very pale yellow powder.

U.V. (methanol): $\lambda_{max}$: 222 and 312 nm

I.R. (KBr): 3400, 2500, 1640, 1600, 1530, 1480, 1350, 1300, 1120, 1050, 880, 810, 740 and 700 cm$^{-1}$ Elementary analysis: Calculated (%) for $C_{16}H_{62}N_6O_{13}$: C: 67.39; H: 5.75; N: 7.73 Found: C: 67.09; H: 5.96; N: 7.76

EXAMPLE 2

A suspension of 93.9 g of benzidamine hydrochloride and 69.6 g of disodium chromoglycate in 400 ml of methanol was heated to reflux. After two hours at reflux, the sodium chloride formed was removed by filtration. The methanol was removed in vacuo and 135.4 g of a fine powder similar to that of the previous Example was obtained.

What is claimed is:

1. A chromoglycic acid derivative having the structural formula I:

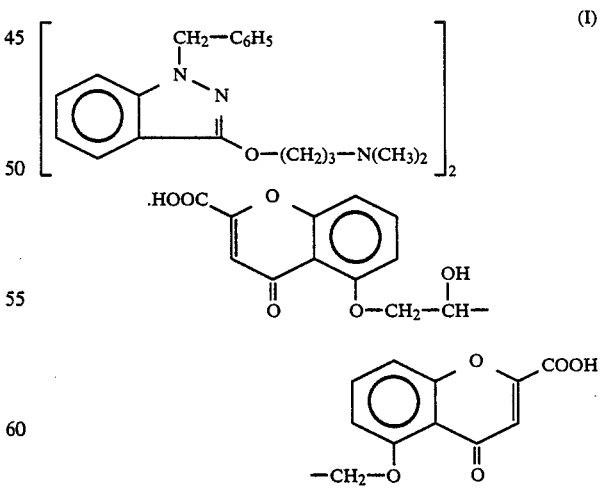

* * * * *